United States Patent [19]

Bouge et al.

[11] Patent Number: 4,622,459
[45] Date of Patent: Nov. 11, 1986

[54] TONOMETER WITH OPTICAL SENSING AND VARIABLE ATTENUATOR

[75] Inventors: Harry A. Bouge, Project City; Tim O. Haley, Central Valley, both of Calif.

[73] Assignee: Professional Technologies Corp., Redding, Calif.

[21] Appl. No.: 638,047

[22] Filed: Aug. 6, 1984

[51] Int. Cl.⁴ ............................................. H01J 40/14
[52] U.S. Cl. .................................. 250/214 A; 330/284
[58] Field of Search .................. 250/214 AL, 214 A; 330/261, 269, 284; 307/311; 73/705; 33/174 L

[56] References Cited

U.S. PATENT DOCUMENTS 3,992,926 11/1976 Berryhill .............................. 364/415

OTHER PUBLICATIONS

Tassell, *Electronic Engineering*, vol. 52, No. 637, p. 23, Mid-Apr. 1980.
Penfold, *Radio and Electronics Constructor*, vol. 33, No. 10, pp. 604–608, (particularly FIG. 1).

*Primary Examiner*—David C. Nelms
*Assistant Examiner*—James G. Gatto
*Attorney, Agent, or Firm*—Willis E. Higgins; Edward B. Gregg

[57] ABSTRACT

An optical sensor system (10) in the form of a hand held tonometer probe has an infrared emitting diode (34) and a phototransistor detector (36) positioned to receive light from the diode (34). A rod (18) serves as a variable attenuator to intercept a portion of light from the diode (34) directed at the detector (36). A signal level detecting amplifier (104) is coupled to the detector (36) to receive an output signal from the detector (36) in response to light from the diode (34) received by the detector (36). The amplifier (104) has a non-inverting input (102) and an inverting input (106). The amplifier (104) receives the output signal from detector (36) at non-inverting input (102). A +5 volt reference potential is connected through a variable resistor (110) and a resistor (108) to establish a bias at the inverting input (106) which is approximately equal to signal levels supplied by the detector (36) to the non-inverting input (102). Rod (18) is movably mounted in housing portion (28) by a spring assembly (24) bonded to housing portion (28) by epoxy (26). Spring assembly (24) has planar rings (40, 42 and 44) encircling the rod (18). Planar springs (52, 54 and 56) extend from the rings (40, 42 and 44) and have their distal ends fixedly attached to the rod (18). The low noise amplifier and interface circuit (72) provides an output proportional to the displacement of rod (18) during pressure measurements.

13 Claims, 8 Drawing Figures

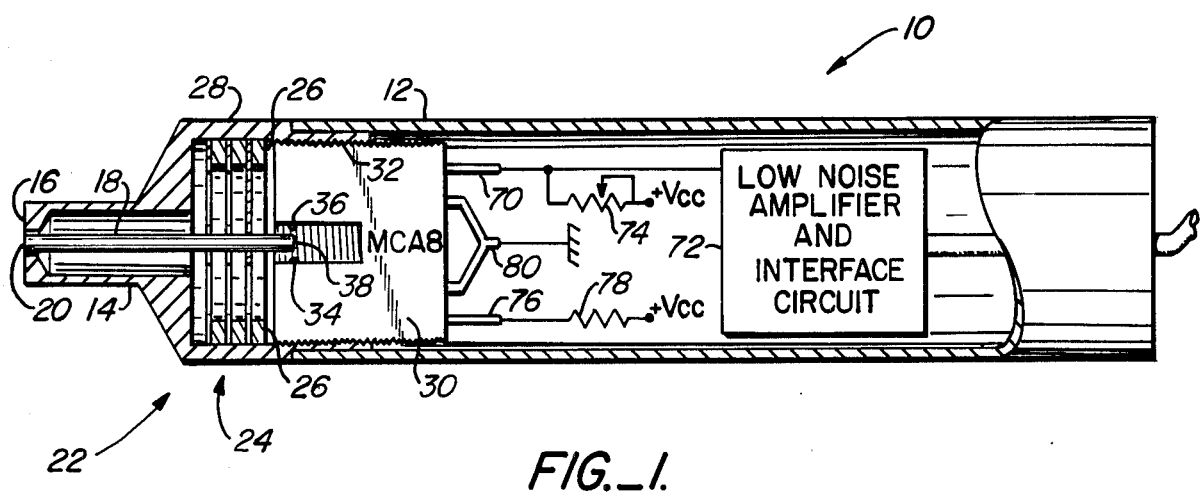
FIG._1.
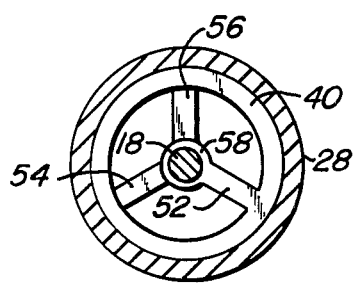
FIG._3.
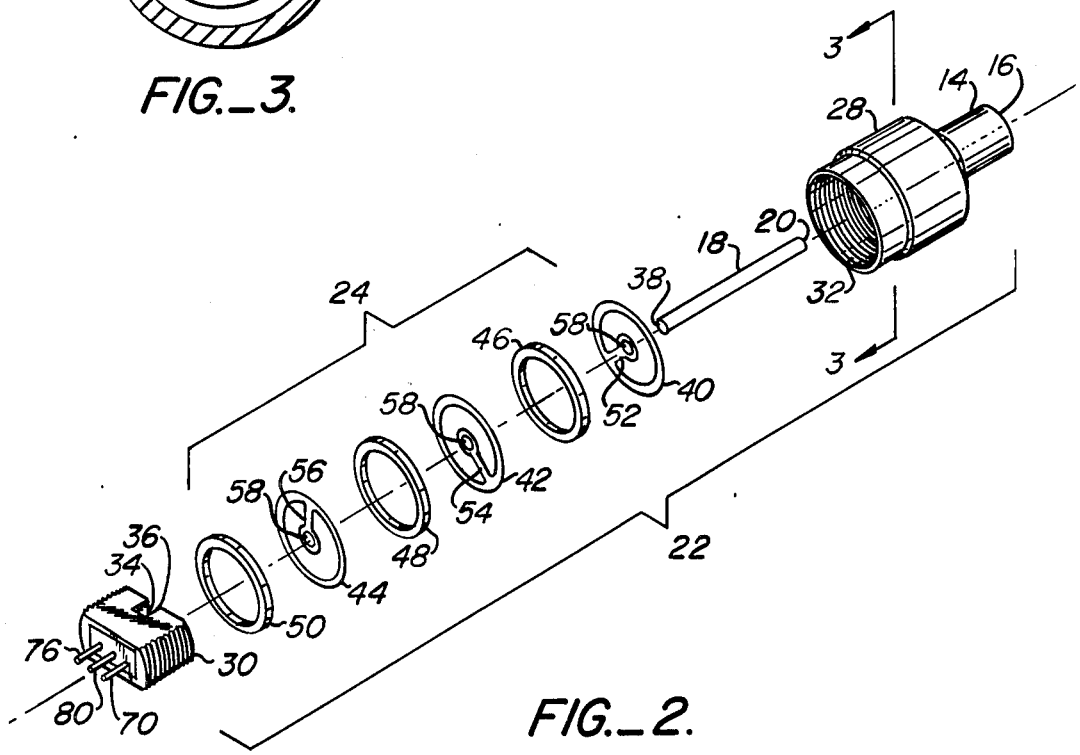
FIG._2.

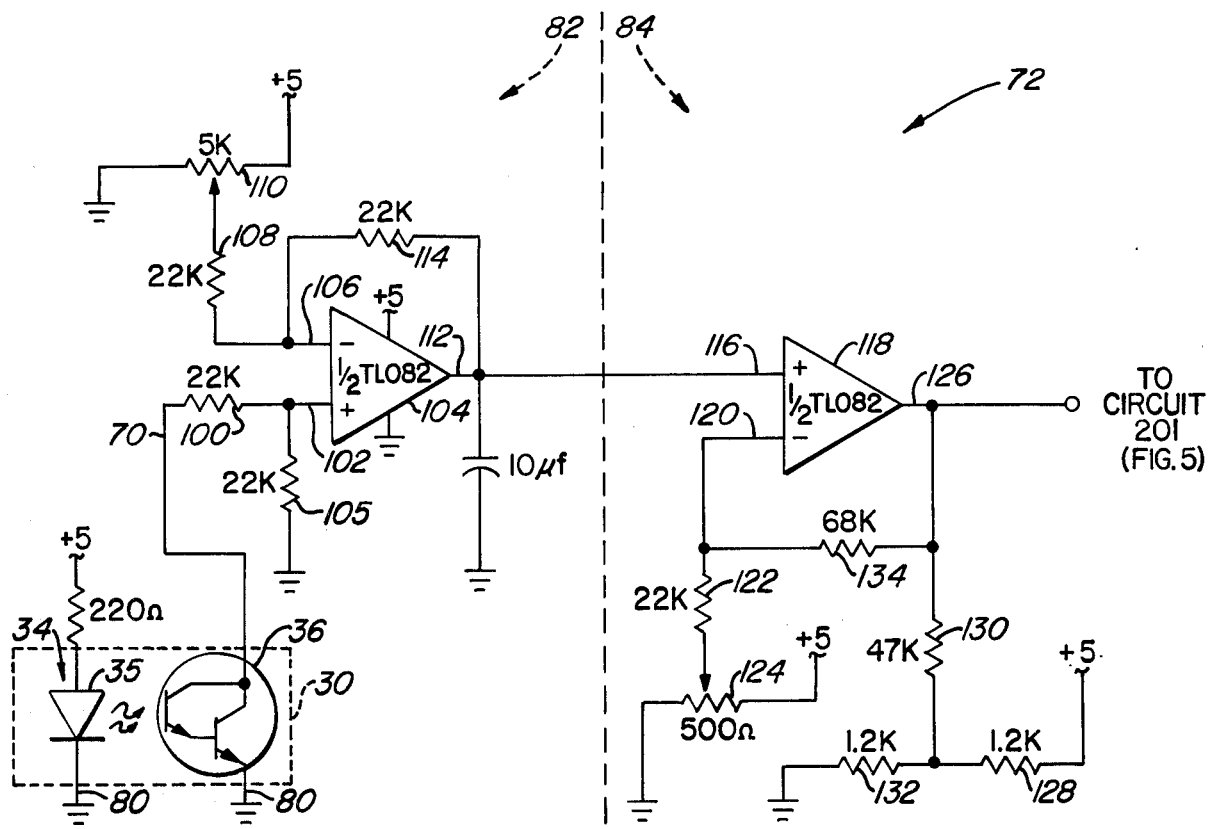
FIG._4.
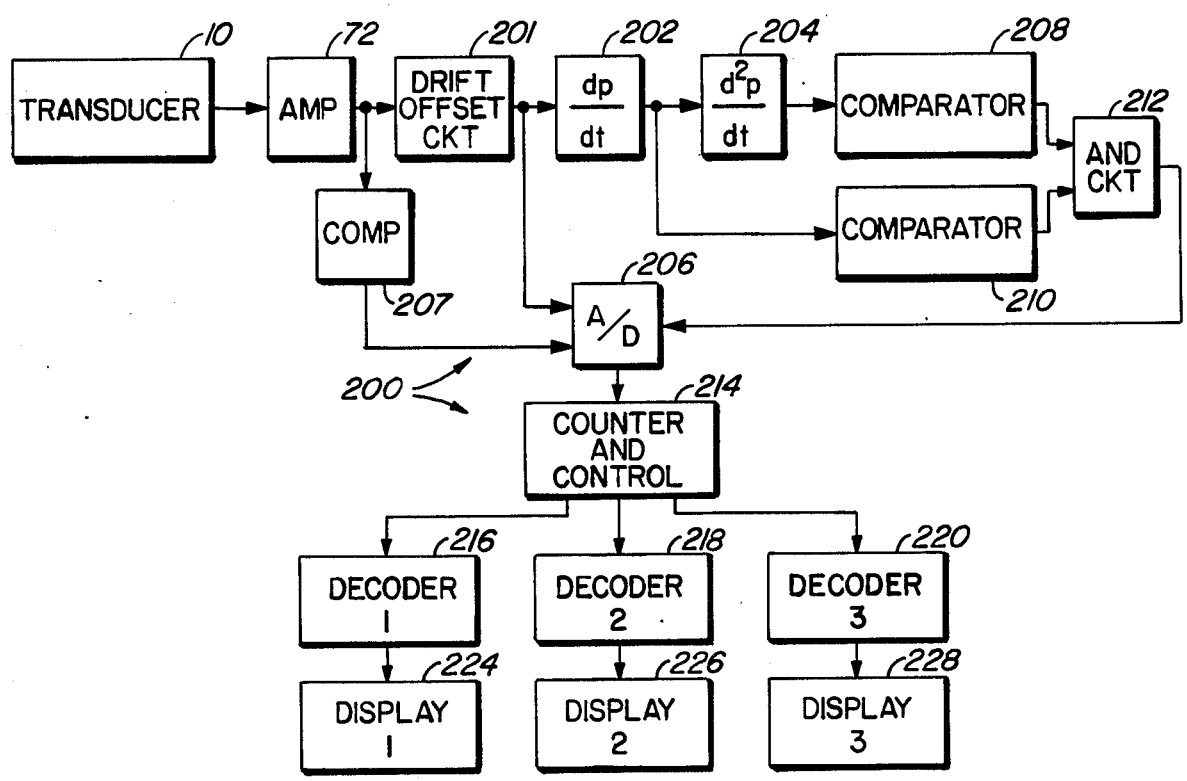
FIG._5.

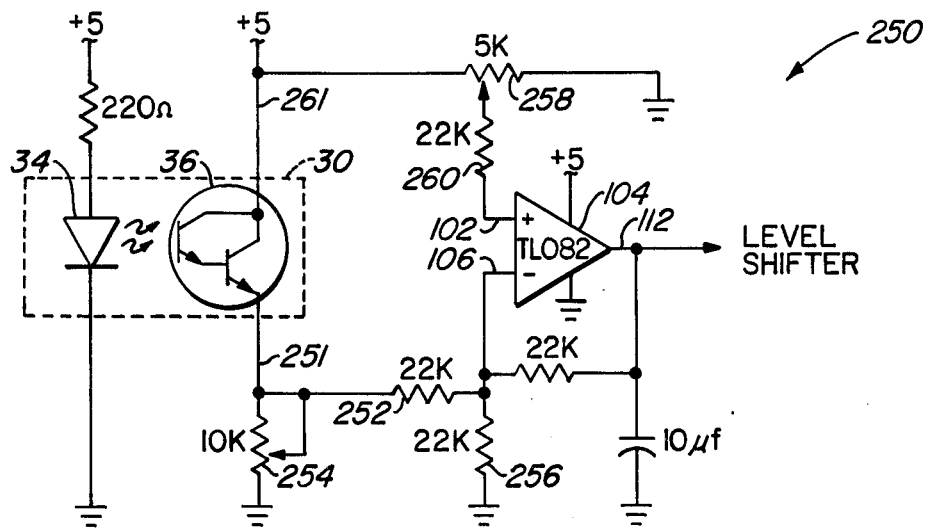
FIG._6.
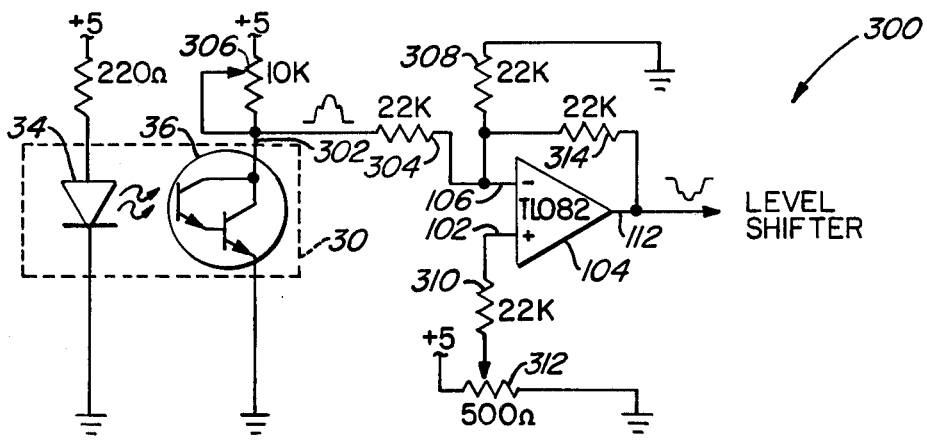
FIG._7.
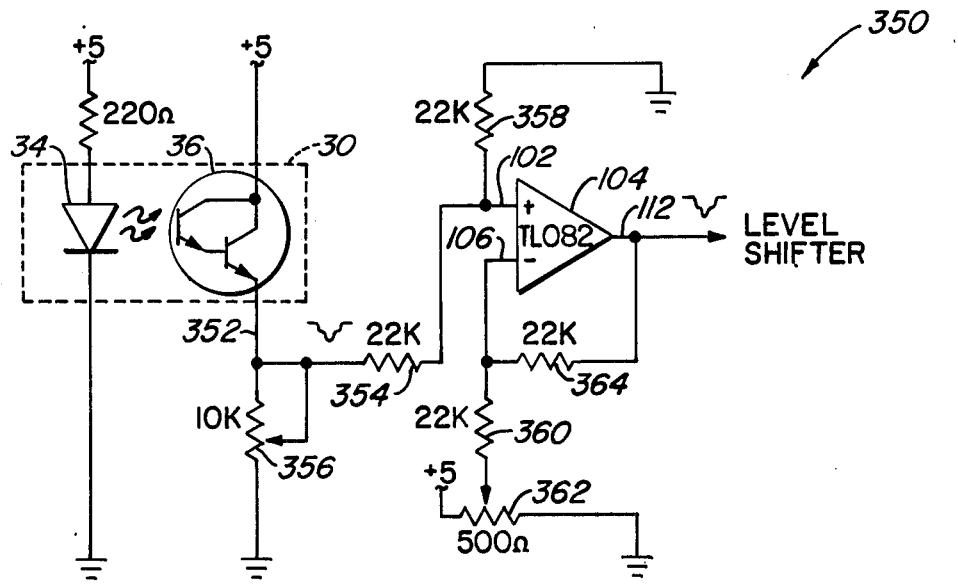
FIG._8.

TONOMETER WITH OPTICAL SENSING AND VARIABLE ATTENUATOR

BACKGROUND OF THE INVENTION

1. Field of the Invention

This invention relates to an improved form of a tonometer in which an optical sensing system is used to measure pressure exerted on a probe. It also relates to an improved optical sensing system especially adapted for use in such a tonometer. More particularly, it relates to an improved hand held pressure probe for use in a tonometer of the applanation type and to a sensing system for use with the probe that detects signal levels generated by the probe in an improved manner.

2. Description of the Prior Art

Tonometers of the applanation type employing a hand held probe having a tip which is applied to the cornea of the eye or other surface of a body having an internal pressure to be measured are known in the art. For example, U.S. Pat. No. 3,992,926, issued Nov. 23, 1976 to Berryhill, discloses a tonometer of this type, which is commercially available from the assignee of this application. The probe of the Berryhill tonometer incorporates a movable rod which is displaced by intraocular or other internal pressure. The rod is connected to a capacitor structure, the capacitance of which is altered by the displacement of the rod. Measurement of the capacitance change is used to provide a display of the pressure being measured.

Due to its ease of use by personnel without specialized training, the Berryhill tonometer has achieved substantial acceptance in the marketplace. However, fabrication of the capacitor structure in this probe is somewhat difficult, due to the necessity of providing carefully fabricated capacitor plates at a predetermined spacing of about 0.001 inch. Such tonometer probes incorporating capacitive elements are also somewhat sensitive to damage by shock, such as when dropped or subjected to other impact. Relatively low yields are obtained in fabrication of these probes due to dust, moisture and capacitor plate misalignment. Dust and moisture also contribute to failure in use.

A variety of optical sensing devices are also known in the art. For example, commercially available source and detector assemblies (SDAs), incorporating infrared-emitting diodes and phototransistors, are obtainable from General Instruments Corporation under the designation MCA or Texas Instruments, Incorporated, under the designation TIL. As employed in the prior art, such SDAs are generally utilized in systems where the presence or absence of signal outputs are detected to establish an ON or OFF state, and determining the signal level is not necessary. In those applications where signal level output from the SDAs is required, two signal level detecting amplifiers have been required, with a non-inverted signal input being provided to one of the amplifiers and an inverted signal input being provided to the other amplifier. Prior art attempts to sense the signal level outputs with a single amplifier have been unsuccessful due to the presence of excessive noise in the amplifier output. The necessity of utilizing two amplifiers has prevented the use of such SDAs in situations where a limited amount of space is available for the signal level determining circuit.

SUMMARY OF THE INVENTION

Accordingly, it is an object of this invention to provide an optical sensing system in which a single amplifier may be utilized to sense output signal levels from an optoelectronic sensor.

It is another object of the invention to provide such an optical sensing system in which noise level in an output from the single amplifier is reduced.

It is a further object of the invention to provide a probe for an applanation tonometer in which a capacitive element used to sense displacement is eliminated.

It is still another object of the invention to provide such a probe having an increased resistance to damage by shock, dust or moisture.

The attainment of the these and related objects may be achieved through use of the novel optical sensor system and tonometer probe herein disclosed. An optical sensor system in accordance with the invention has a light source and a detector positioned to receive light from the light source. A variable attenuator is positioned to intercept a portion of the light from the light source directed at the detector. A signal level detecting amplifier is coupled to the detector to receive an output signal from the detector in response to light from the light source received by the detector. The signal level detecting amplifier has a non-inverting input and an inverting input. The signal level detecting amplifier is connected to receive the output signal from the detector at one of the inputs. A means is connected to the other input of said signal level detecting amplifier to establish a bias voltage at the other input which is approximately equal to signal levels supplied by the detector to the one input of the signal level detecting amplifier. As used herein, the term "approximately equal" means that the input signal and the bias voltage should be constrained to be within about 80 percent of one another. In one embodiment of the invention, the signal level detecting amplifier receives the output signal from the detector at the non-inverting input and the bias voltage at the inverting input. In another embodiment of the invention, the signal level amplifier is connected to receive the output signal from the detector at the inverting input and the biasing means is connected to establish the bias voltage at the non-inverting input.

In another aspect of the invention, a tonometer probe has a housing. A rod is movably mounted within the housing and has an end extending from the housing to contact a flexible surface of a body, such as a cornea of an eye, having an internal pressure to be measured, such as intraocular pressure. A spring assembly is fixedly attached to the housing relative to the rod. The spring assembly includes at least one planar ring encircling the rod. The assembly has a plurality of planar springs extending from the at least one planar ring. The planar springs have their distal ends fixedly attached to the rod. The probe includes a means for sensing an extent of displacement of the rod. Preferably the sensing means is optical and includes a light source and a detector positioned to receive light from the light source, the light source and detector being arranged in the housing so that displacement of the rod intercepts a light path between the source and detector to an extent dependent on displacement of the rod.

While the optical sensor system and the tonometer probe of this invention can each be used separately, in a preferred embodiment of the invention, they are used together. The optical sensing system allows a signal level which is dependent on displacement of the rod to be reliably measured in a miniaturized system which can be incorporated within a handheld tonometer probe. The tonometer probe construction of this invention is much easier to fabricate than prior art tonometer probes of the applanation type.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a cross-section view of a tonometer probe in accordance with the invention.

FIG. 2 is an exploded perspective view of a portion of the tonometer probe shown in FIG. 1.

FIG. 3 is a plan view of a portion of the tonometer probe shown in FIGS. 1 and 2.

FIG. 4 is a circuit schematic of a detector circuit incorporated in the tonometer probe of FIGS. 1 and 2.

FIG. 5 is a block diagram of a tonometer system in accordance with the invention.

FIG. 6 is a circuit schematic of another embodiment of a detector circuit for use in the tonometer probe of FIGS. 1 and 2.

FIG. 7 is a circuit schematic of a third embodiment of a detector circuit for use in the tonometer probe of FIGS. 1 and 2.

FIG. 8 is a circuit schematic of a fourth embodiment of a detector circuit for use in the tonometer probe of FIGS. 1 and 2.

DETAILED DESCRIPTION OF THE INVENTION

Turning now to the drawings, more particularly to FIGS. 1-3, there is shown a tonometer probe 10 in accordance with the invention. The probe 10 has a generally pencil-shaped housing 12. Housing 12 has a diameter and a length designed for permitting the probe 10 to be handheld, and has an end 14 of reduced diameter provided with an annular flat applanating surface 16 having an outside diameter suitable for applanating the cornea of an eye. A plunger rod 18 is movably mounted within the housing 12. Rod 18 has a planar surface 20, which is essentially in the plane of the surface 16, but movable with respect thereto a small distance, such as a few microns. The portion of reduced diameter 14 of housing 12 and the rod 18 are a part of transducer assembly 22, which is enclosed by an end portion 28 of the housing 12 with the portion of reduced diameter 14 extending from the remainder of portion 28, as shown.

Rod 18 is fixedly attached to spring assembly 24, which is bonded by means of epoxy 26 to the interior of portion 28 of the housing 12. A commercially available SDA assembly 30 is also fixedly attached to the portion 28 of housing 12, by screw threads 32. The SDA assembly 30 has an infrared-emitting diode 34 and a phototransistor 36 positioned to receive infrared light from the diode 34. The SDA assembly 30 is positioned within the housing portion 28 so that end 38 of the rod 18 will intercept the light path between diode 34 and detector 36, with the extent of the interception being determined by the extent of movement of the rod 18 when end 20 is placed in contact with the cornea of a patient's eye during use of the probe 10.

Further details of the tonometer transducer assembly 22 are shown in FIG. 2. As shown, the spring assembly 24 consists of three planar rings 40, 42 and 44, formed from a suitable spring metal and separated by aluminum ring spacers 46, 48 and 50. Each of the rings 40, 42 and 44 has a planar spring 52, 54 and 56, respectively, extending from the ring inward to the center of a circle formed by each ring 40, 42 and 44. Each spring 52, 54 and 56 has an aperture 58 through which the rod 18 extends to reach the SDA assembly 30.

In fabrication of the tonometer transducer assembly 22, the spring assembly 24 is stacked in the relationship shown in FIG. 2 to give the configuration best shown in FIG. 3, with each of the springs 52, 54 and 56 being equally spaced around the circumference of the circle formed by the rings 40, 42 and 44. Rod 18 is inserted through the apertures 58 and bonded to the spring 52 by means of a cyanoacrylate adhesive, such as Loctite 404, obtained from Loctite Corporation, Newington, Mass. The spring assembly 24 and rod 18 are then positioned within housing portion 28 so that end 20 of the rod 18 extends from reduced diameter portion 14 of the housing 12. Spring assembly 24 is then epoxy bonded to the interior of housing portion 28. SDA assembly 30 is screwed into housing portion 28 to a sufficient extent so that end 38 of the rod 18 is in abutting relationship to the light path between diode 34 and detector 36.

In practice, the SDA assembly 30 may be implemented with a MCA8 type SDA assembly, obtainable from General Instruments Corporation or a TIL143, TIL144, TIL147A, TIL148A, TIL158, TIL159, TIL167-1, TIL167-2, TIL169-1 or TIL169-2 SDA assembly, obtainable from Texas Instruments Incorporated. With these SDA assemblies 30, the detector 36 is a single N-P-N silicon phototransistor. Alternatively, the SDA assembly 30 may be implemented with TIL145, TIL146, TIL160, TIL161, TIL168-1, TIL168-2, TIL170-1 or TIL170-2 type SDA assemblies, in which cases the photodetector 36 is an N-P-N silicon Darlington phototransistor pair.

Pin 70 of the SDA assembly 30 is connected to a low noise amplifier and interface circuit 72 (see also FIG. 4) to provide an output signal from the SDA assembly 30 to the circuit 72 which varies, based on the extent rod 18 blocks the light path between diode 34 and detector 36. Pin 70 is connected to a collector electrode of a phototransistor comprising the detector 36. When implemented with the MCA8 type SDA assembly, the pin 70 is also connected to a source of +Vcc potential, for example 5 volts, through a 10K ohm variable resistor 74. Pin 76 is connected to the Vcc potential by a 220 ohm resistor 78. Pin 80, connected to the cathode of the diode 34 and to the emitter of detector 36, is grounded.

Further details of the low noise amplifier and interface circuit 72 are shown in FIG. 4. The circuit 72 includes a low noise amplifier portion 82 and a level shifter interface portion 84. Pin 70 is connected through a 22K ohm resistor 100 to a non-inverting input terminal 102 of an operational amplifier circuit 104. The input 102 is also connected to ground through a 22K ohm resistor 105. A signal input at terminal 102 varies between about 1.16 volt and 2.5 volt with respect to circuit ground, depending on the position of rod 18. Inverting input terminal 106 of the operational amplifier 104 is connected through a 22K ohm resistor 108 and a 5K ohm variable resistor 110 to the +5 volt Vcc potential. Output terminal 112 of the operational amplifier 104 is connected through 22K ohm resistor 114 to the inverting input terminal 106. The bias level at inverting input 106 of the operational amplifier is kept within about 80% of the signal level at non-inverting terminal 102.

Table 1 shows voltage levels at the four points 70, 102, 106 and 112 of the low noise amplifier circuit 82 in FIG. 4. The first column of voltages are obtained with end 38 of the rod 18 at an arbitrary starting point, in this case, blocking half of the light path between diode 34 and the detector 36. The apparatus is calibrated so that the end 38 is so located when no force is being applied to rod 18 from an eyeball or other source of pressure to be measured. Columns 2-6 show voltages measured as rod end 38 moves further into the light path between diode 34 and detector 36, with column 6 representing full blockage of the light path. As can be seen, the circuit 82 operates to maintain the bias voltage at node 106 of the circuit approximately equal to the signal voltage at node 102 of the circuit 82.

TABLE 1

| Node  | Voltages |        |        |        |        |        |
|-------|----------|--------|--------|--------|--------|--------|
| 70 *  | 2.34 v   | 2.44 v | 2.54 v | 3.02 v | 4.00 v | 4.96 v |
| 102 * | 1.17     | 1.22   | 1.27   | 1.51   | 1.99   | 2.47   |
| 106 * | 1.26     | 1.27   | 1.27   | 1.32   | 1.89   | 2.45   |
| 112 * | 1.43     | 1.43   | 1.43   | 1.53   | 2.64   | 3.74   |

By setting the level at input terminal 106 in this manner with respect to the signal level at terminal 102, a low noise output signal is obtained at output terminal 112 of the operational amplifier 104. Configuring the low noise amplifier 82 of the circuit 72 in this manner means that only a single operational amplifier 104 is required in order to obtain a suitable output signal at terminal 112, based on the position of rod 18.

The output signal at terminal 112 from operational amplifier 104 is supplied to the non-inverting input terminal 116 of operational amplifier circuit 118 in level shifter portion 84 of the circuit 72. The inverting input terminal 120 of the operational amplifier 118 is connected to the +5 volt Vcc potential through 22K ohm resistor 122 and 500 ohm variable resistor 124. The signal at terminal 16 varies as shown in Table I. The signal at terminal 120 is also maintained within about 80% of the signal at terminal 116. Output terminal 126 of the operational amplifier 118 is connected to drift offset circuit 201 of tonometer system 200 (FIG. 5). The output terminal 126 is also connected to the +5 volt Vcc potential through 1.2K ohm resistor 128 and 47K ohm resistor 130. Resistor 128 and a second 1.2K ohm resistor 132 divide the +5 volt Vcc voltage to provide a reference voltage of 2.5 volt at the input to resistor 130. Output terminal 126 is also connected to input terminal 120 through a 68K ohm resistor 134.

In practice, an anode 35 of the diode 34 is connected to the +5 volt Vcc potential through a 220 ohm resistor 134. The operational amplifiers 104 and 118 may be implemented with a single dual operational amplifier integrated circuit, such as a TL082 type dual operational amplifier integrated circuit, obtainable from Texas Instruments.

In operation of the circuit 72, noise on the input terminal 102 of the amplifier portion 82 is eliminated when the inverting input terminal 106 has an approximately equal voltage level to the non-inverting input terminal 102. The output signal at terminal 112 is virtually noise free when this condition exists. The operational amplifier 104 appears to be shut down except during a time when a signal is present at input terminal 102 and exceeds a threshold. The operation of the operational amplifier 104 is somewhat analogous to that of a class B amplifier under these conditions. The gain of the operational amplifier 104 is controlled by the variable resistor 110, which will ensure that the output terminal 112 of the circuit can be set for a specific amplitude signal with a known input pressure to the probe 10.

The second operational amplifier 118 in the circuit 72 provides the level shifting function of portion 84 so that the circuit 72 can be connected to the rest of the tonometer system 200 shown in FIG. 5. The low noise amplifier and interface circuit 72 is connected through a drift offset circuit 201 to a first one 202 of a pair of series coupled differentiating circuits 202 and 204 and to an analog-to-digital converter 206 through a comparator circuit 207. Circuits 202 and 204 are also respectively coupled by means of a pair of comparator circuits 208 and 210, in series with a dual input AND and flipflop circuit 212 to the analog to digital converter 206. Converter 206 is in turn coupled through a counter and control circuit 214 to a plurality of decoder driver/latch circuits 216, 218, and 220, which drive an equal number of display circuits 224, 226, and 228.

Other than in the construction and operation of the tonometer probe transducer 10 and the low noise amplifier and interface circuit 72, and as set forth above, the construction and operation of the tonometer system 200 in FIG. 5 is the same as shown and described in the above referenced Berryhill, U.S. Pat. No. 3,992,926, the disclosure of which is hereby incorporated by reference herein.

FIG. 6 is another embodiment of a low noise amplifier circuit 250 in accordance with the invention. In the circuit 250, the emitter 251 electrode of the phototransistor pair 36 in the SDA 30 is connected to the inverting input 106 of the operational amplifier 104 through a 22K ohm resistor 252. The emitter is also connected through 10K ohm variable resistor 254 to ground, and the input 106 is connected to ground through 22K ohm resistor 256. The non-inverting input 102 of the operational amplifier 104 is connected between +5 volt Vcc potential and ground through 5K ohm variable resistor 258 and 22K ohm resistor 260. The collector terminal 261 of the transistor pair 36 is also connected to the +5 volt Vcc potential.

In the circuit 250 of FIG. 6, the bias voltage at non-inverting terminal 102 of the operational amplifier 104 is also maintained approximately equal to signal levels supplied by the SDA 30 to the inverting input 106, i.e., within about 80 percent of the signal level at the inverting input 106. For use with the rest of the system 200 in FIG. 5 in place of the amplifier portion 84 shown in FIG. 5, the output signal at terminal 112 of the operational amplifier 104 is later inverted. In other respects, the construction and operation of a tonometer system incorporating the circuit 250 is the same as explained above in connection with FIGS. 1-5.

Table II shows voltages at nodes 251, 106, 102 and 112 of the FIG. 6 low noise amplifier circuit 250. As in the case of Table I, the first column of voltages shows the values obtained with end 38 of rod 18 positioned approximately midway across the light path between the diode 34 and transistor pair 36, with no pressure applied against end 20 of the rod 18. Remaining columns 2-8 show the voltages obtained with increased blockage of the light path, with column 8 representing full blockage of the light path by rod 18. As in the case of Table I, the voltages shown are with respect to circuit ground.

TABLE II

| Node | Voltages | | | | | | | |
|---|---|---|---|---|---|---|---|---|
| 251 * | 2.41 v | 2.21 v | 2.00 v | 1.38 v | 1.20 v | 1.00 v | .80 v | 0.00 v |
| 106 * | 1.27 | 1.20 | 1.14 | .94 | .91 | .91 | .91 | .90 |
| 102 * | 1.05 | 1.05 | 1.05 | 1.05 | 1.05 | 1.05 | 1.05 | 1.05 |
| 112 * | 1.40 | 1.40 | 1.41 | 1.45 | 1.52 | 1.70 | 1.90 | 2.69 |

FIG. 7 shows another embodiment of a low noise amplifier circuit 300 in accordance with the invention. The collector electrode 302 of transistor pair 36 is connected through 22K ohm resistor 304 to inverting input terminal 106 of the operational amplifier 104. Electrode 302 is also connected through a 10K ohm resistor 306 to the +5 volt Vcc potential. Terminal 106 of the amplifier 104 is also connected to ground through a 22K ohm resistor 308. Non-inverting input terminal 102 of the amplifier 104 is connected through 22K ohm resistor 310 and 500 ohm variable resistor 312 to ground and the +5 volt Vcc potential. Output 112 of the amplifier 104 is connected to inverting input 106 through 22K ohm resistor 314. As in the case of the FIGS. 4 and 6 circuits, the bias voltage applied to terminal 102 and the signal input from detector 36 applied to terminal 106 are kept approximately equal.

Table III below shows the voltages at nodes 302, 106, 102 and 112 with various signal levels from the detector 36. Column 1 shows the voltages with no pressure applied to rod 18, and columns 2-9 show the corresponding voltages with increasing pressure and hence, increasing blockage of the light path between diode 34 and the transistor pair 36.

TABLE III

| Nodes | Voltages | | | | | | | |
|---|---|---|---|---|---|---|---|---|
| 302 * | 2.40 v | 2.50 v | 2.60 v | 2.90 v | 3.01 v | 3.49 v | 4.00 v | 4.48 v | 4.99 v |
| 106 * | 2.24 | 2.27 | 2.30 | 2.40 | 2.43 | 2.52 | 2.52 | 2.52 | 2.52 |
| 102 * | 2.54 | 2.54 | 2.54 | 2.54 | 2.54 | 2.54 | 2.54 | 2.54 | 2.54 |
| 112 * | 4.31 | 4.31 | 4.31 | 4.31 | 4.28 | 4.08 | 3.57 | 3.10 | 2.59 |

FIG. 8 shows another low noise amplifier circuit 350 in accordance with the invention, in which the emitter electrode 352 of the transistor pair 36 is connected through 22K ohm resistor 354 to non-inverting input 102 of the operational amplifier 104. The emitter 352 is also connected through a 10K ohm variable resistor 356 to ground. Input 102 is also connected to ground through a 22K ohm resistor 358. Inverting ihput 106 of the amplifier 104 is connected through a 22K ohm resistor 360 and a 500 ohm variable resistor 362 to the +5 Vcc potential and to ground. Output 112 of the amplifier 104 is connected to a level shifter (not shown) and to the inverting input 106 through 22K ohm resistor 364. As in the FIGS. 4, 6 and 7 embodiments, the bias voltage at input 106 and the detector signal input at 102 are maintained approximately equal.

Table IV below shows the voltages obtained at nodes 352, 102, 106 and 112, in the same manner as in Tables I-III.

TABLE IV

| Nodes | Voltages | | | | | |
|---|---|---|---|---|---|---|
| 325 * | 5.00 v | 5.51 v | 4.01 v | 3.50 v | 2.00 v | 1.75 v |
| 102 * | 2.49 | 2.25 | 2.00 | 1.74 | 1.00 | .88 |
| 106 * | 2.30 | 2.19 | 1.90 | 1.58 | .90 | .88 |
| 112 * | 4.32 | 4.09 | 3.51 | 2.89 | 1.51 | 1.45 |

It should now be readily apparent to those skilled in the art that a novel optical sensor system and tonometer probe especially adapted for use in the optical sensor system capable of achieving the stated objects of the invention has been provided. A single operational amplifier 104 is utilized to sense output signal levels from the SDA assembly 30. By maintaining the inverting input 106 of the operational amplifier 102 positive with respect to the non-inverting input 102 which receives the signal from the SDA assembly 30, noise at the output 112 of the operational amplifier 104 is substantially eliminated. This optical sensing system allows elimination of a difficult to fabricate capacitive element previously used to sense displacement of a pressure measuring member of prior art applanation tonometer probes. By eliminating the capacitive element, the tonometer probe of this invention has an increased resistance to damage by shock.

It should further be apparent to those skilled in the art that various changes in form and details of the invention as shown and described may be made. It is intended that such changes be included within the spirit and scope of the claims appended hereto.

What is claimed is:

1. An optical sensor system, which comprises a light source, a detector positioned to receive light from said light source, a variable attenuator positioned to intercept a portion of light from said light source directed at said detector, a signal level detecting amplifier coupled to said detector to receive a first output signal from said detector which varies throughout a range of levels depending on an extent of attenuation by said variable attenuator in response to light from said light source received by said detector, said signal level detecting amplifier having an non-inverting input and an inverting input, said signal level detecting amplifier being connected to receive the output signal from said detector at one of said inputs, and means connected to another of said inputs of said signal level detecting amplifier to establish a bias voltage at said other input, which is within about 80 percent of signal levels supplied by said detector to the one input of said signal level detecting amplifier throughout the range of levels, said signal level detecting amplifier producing a second outut signal which varies continuously throughout the range of levels of the one input signal and proportionally relative to the one input signal levels.

2. The optical sensor system of claim 1 in which said detector is connected to supply the output signal to the non-inverting input of said signal level detecting amplifier and said bias level establishing means is connected to the inverting input of said signal level detecting amplifier.

3. The optical sensor system of claim 1 in which said detector is connected to supply the output signal to the inverting input of said signal level detecting amplifier and said bias level establishing means is connected to the non-inverting input of said signal level detecting amplifier.

4. The optical sensor system of claim 1 in which said bias voltage level establishing means comprises a potential source, a variable resistor connected to said potential source, and a resistor connected between said variable resistor and the inverting input of said signal level detecting amplifier.

5. The optical sensor system of claim 1 in which said light source is an infrared-emitting diode.

6. The optical sensor system of claim 1 in which said detector comprises at least one phototransistor.

7. The optical sensor system of claim 6 in which said detector is a Darlington phototransistor pair.

8. The optical sensor system of claim 1 in which said variable attenuator comprises a spring loaded member positioned to intercept a light path between said light source and said detector, with an amount of the light intercepted being proportional to displacement of said member into the light path.

9. The optical sensor system of claim 8 in which said member has an elongated, cylindrical shape and said variable attenuator includes a spring assembly fixedly attached to a support and including at least one planar ring encircling said rod shaped member, said assembly having a plurality of planar springs extending from said at least one planar ring and having their distal ends fixedly attached to said rod shaped member.

10. The optical sensor system of claim 9 in which said spring assembly is formed from a plurality of the planar rings each having one of the plurality of planar springs, the plurality of planar rings being separated from one another by at least one planar spacer.

11. A low noise signal level detecting amplifier circuit comprising an operational amplifier having a non-inverting input and an inverting input, a source of a signal which varies throughout a range of levels depending on an extent of attenuation by said variable attenuator to be detected connected to one of said inputs, and means connected to another of said inputs to establish a bias voltage at said other input, such that said signal and said bias voltage are within about 80 percent of each other throughout the range of levels, said signal level detecting amplifier producing an output signal which varies continuously throughout the range of levels of the one input signal and proportionally relative to the one input signal levels.

12. The low noise signal level detecting amplifier circuit of claim 11 in which said signal source is connected to supply the signal to be detected to said non-inverting input and said bias voltage establishing means is connected to supply the bias voltage at said inverting input.

13. The low noise signal level detecting amplifier circuit of claim 11 in which said signal source is connected to supply the signal to be detected to said inverting input and said bias voltage establishing means is connected to supply the bias voltage at said non-inverting input.

* * * * *